United States Patent [19]

Rademacher et al.

[11] Patent Number: 6,106,822

[45] Date of Patent: Aug. 22, 2000

[54] HORMONE AND GROWTH FACTOR PHOSPHOGLYCOKINE MIMETICS FROM MYCOBACTERIUM

[75] Inventors: Thomas W. Rademacher; Hugo N. Caro; Graham A. W. Rook, all of London, United Kingdom

[73] Assignee: University College of London, London, United Kingdom

[21] Appl. No.: 08/913,604

[22] PCT Filed: Mar. 20, 1996

[86] PCT No.: PCT/GB96/00669

§ 371 Date: Feb. 2, 1998

§ 102(e) Date: Feb. 2, 1998

[87] PCT Pub. No.: WO96/29425

PCT Pub. Date: Sep. 26, 1996

[30] Foreign Application Priority Data

Mar. 21, 1995 [GB] United Kingdom .................... 9505658

[51] Int. Cl.[7] .............................. A61K 45/00; C12N 1/00; C12N 1/20; C12P 1/04
[52] U.S. Cl. ..................... 424/85.1; 424/282.1; 435/170; 435/253.1; 435/863
[58] Field of Search ................................ 424/85.1, 282.1; 435/170, 253.1, 863

[56] References Cited

FOREIGN PATENT DOCUMENTS

WO A 91 02542 3/1991 WIPO .
WO A 93 16727 9/1993 WIPO .

OTHER PUBLICATIONS

Chemical Abstracts, vol. 120, No. 25, Jun. 20, 1994 Columbus, Ohio, US; abstract No. 315887v, T W Rademacher et al.; "inositolphosphoglycan second messengers" p. 106; XP002006591 see abstract & Braz. J. Med. Biol. Res., vol. 27, No. 2, 1994, pp. 327–341.

Chemical Abstracts, vol. 123, No. 23, Dec. 4, 1995 Columbus, Ohio, US; abstract No. 312104p, R Hernandez–Pando et al.: "Adrenal changes in murine pulmonar tuberculosis; a clue to pathogenesis?" p. 724; XP002006592 see abstract & FEMS Immunol. Med. Microbiol., vol. 12, No. 1, 1995, pp. 63–72.

*Primary Examiner*—David M. Naff
*Assistant Examiner*—Deborah K. Ware
*Attorney, Agent, or Firm*—Nixon & Vanderhye

[57] ABSTRACT

A hormone or growth factor mimetic second messenger is derived from a microorganism of the genus Mycobacterium, suitably *M. vaccae*. The mimetic second messenger may mimic the action of insulin, ACTH, NGF, EGF, FGF, TGFβ or HGF. Further, methods of treating type I or type II diabetes mellitus, polycystic ovary syndrome, central nervous system damage, hepatic damage, alcohol abuse, drug sensitivity, tissue damage, adrenal atrophy, etc., are also disclosed. The methods are carried out by administering the mimetic second messenger to a patient in need thereof.

10 Claims, 5 Drawing Sheets

HORMONE AND GROWTH FACTOR PHOSPHOGLYCOKINE MIMETICS FROM MYCOBACTERIUM

BACKGROUND

1. Field of the Invention

The present invention relates to second messengers which mimic the action of insulin and other mammalian growth factors and hormones.

2. Related Art

Non insulin-dependent diabetes mellitus is one of the most common metabolic disorders in the industrial world. Associated with the disorder are dyslipidemias, atherosclerosis, hypertension, cardiovascular disorders and renal dysfunction. Obesity constitutes the greatest risk factor for the disease. Two physiological defects that lead to the development of diabetes are tissue resistance to the effects of insulin and altered secretion of insulin.

In order for new treatments of this disorder to be developed it is necessary to understand the specifics of the insulin signalling pathways and other signalling pathways which may interfere with insulin action. It has recently been demonstrated that low molecular weight phosphorylated inositolglycans (IPGs), are released upon insulin stimulation in a tissue-specific manner. These compounds are in the family of phosphoglycokines (PGK), defined as biologically active low molecular weight compounds containing phosphorylated carbohydrates. The tissue-derived IPGs mediate some of the actions of insulin. Such insulin-mimetics have therapeutic potential in that they could:

(i) substitute for insulin either as a parenteral or oral treatment in patients with diabetes where the primary pathology relates either to decreased synthesis (type I diabetes) or lack of bioavailable insulin (defects in conversion of proinsulin to insulin or in the formation of anti-insulin antibodies).

(ii) be used to treat patients with tissue insulin resistance, which is seen in many cases of adult onset or type II diabetes.

(iii) be used to treat or prevent complications of diabetes including dyslipidemias, atherosclerosis, hypertension, cardiovascular disorders and renal dysfunction. It has further been found that the IPGs are able to cross the blood brain barrier and affect cerebral glucose and energy metabolism. Since insulin itself has limited ability to cross the blood brain barrier, release of the compounds into the circulation following insulin stimulation may be crucial in the control of energy metabolism in the brain. In clinical trials, tissue-derived IPGs have been shown to be effective in reversing age-associated memory loss and in providing a protective effect under cerebral hypoxic conditions.

As detailed below, the inositolphosphoglycan second messenger signal transduction effect has also been shown to be functionally relevant for the signalling of other growth factors, including fibroblast growth factor (important in wound healing), transforming growth factor β (important in autoimmunity) and hepatocyte growth factor (also known as scatter factor), that together with other growth factors, is important for the regeneration of liver tissue following damage by infection, alcohol abuse, drug sensitivity, or autoimmunity.

SUMMARY OF THE INVENTION

The present invention provides a valuable source of phosphoglycokines (PGK) which mimic the activity of the tissue-derived IPGs, which are otherwise not readily available. Only very small quantities of the IPGs can be isolated from mammalian tissues. Since the IPGs are non-protein in composition, they cannot be produced by recombinant DNA technology. Synthetic chemistry approaches are complicated by the current lack of structural details of the tissue-derived IPGs and the complications associated with oligosaccharide syntheses.

Immunotherapy with *M. Vaccae*

We have previously described the use of antigenic and/or immuno regulatory material derived from *Mycobacterium vaccae* in the treatment of tuberculosis (see, for example, British Patent No. 2156673 and U.S. Pat. No. 4,724,144). In our International Patent Application No. PCT/GB90/01169 (publication No. WO91/01751), we have described the use of the same material for immunoprophylactic treatment against AIDS, i.e. for increasing the period between infection by HIV and development of AIDS.

*Mycobacterium vaccae* has also been shown to have therapeutic potential as a treatment for patients infected both with Human Immunodeficiency Virus (HIV) and tuberculosis as described by Stanford, J. L. in AIDS (1993) 7, pp 1275–1277. The mechanism of the immunotherapeutic effect is not fully established, but may relate to the ability of compounds within the organism to evoke a Th1 pattern of T cell response to proteins rich in epitopes shared between mycobacterial species as described by Boyden, S. V. in J. Immunol. (1955), 75, pp 15. Human homologues of several of these proteins are implicated in human autoimmune diseases such as rheumatoid arthritis and perhaps also in schizophrenia, and *M. vaccae* may also have relevant immunoregulatory properties in these conditions.

DETAILED DESCRIPTION OF THE INVENTION

Figure 1:
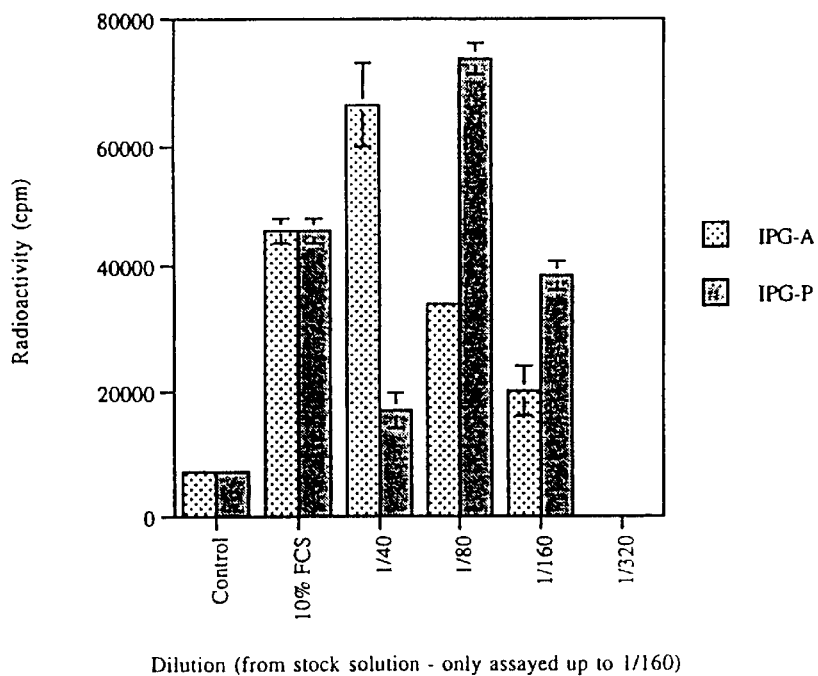
FIG. 1 is a bar graph showing both the liver A and P-type IPGs were able to stimulate proliferation of the fibroblasts in serum free medium.

We have unexpectedly found that phosphoglycokines (PGK) which co-purify with insulin-mimetic inositolphosphoglycans (IPG) from rat or human liver can be obtained from cultures of *Mycobacterium vaccae*. The *M. vaccae* derived products are able to mimic the action of mammalian IPG second messengers in the following ways:

(i) stimulation of EGF(Rc) transfected 3T3 cells, (ii) stimulation of pyruvate dehydrogenase phosphatase activity, (iii) inhibition of cAMP dependent protein kinase activity, and (iv) stimulation of lipogenesis in isolated adipocytes.

It is also probable that the *M. vaccae* derived products modulate steroid metabolism in adrenal cells.

It is clear that *M. vaccae* and related strains of mycobacteria are a source of PGKs which either mimic the activity of, or are very similar in structure to, the IPG type of PGK second messengers present in mammalian tissues. Previously, such second messengers could only be isolated in extremely small quantities from mammalian tissues, such as liver. We have surprisingly found that compounds extracted from *M. vaccae* mimic the action of the IPG second messengers. This provides advantages over material derived from liver tissue, in both ease of extraction and in the quantities of messenger which may be obtained.

The present invention accordingly provides a hormone and growth factor mimetic second messenger derived from a mycobacterium, preferably from *Mycobacterium vaccae*. The mimetic second messenger may mimic the action of a number of hormones and growth factors. For example, the mimetic second messenger may mimic the action of insulin, adrenocorticotropic hormone (ACTH), nerve growth factor (NGF), epidermal growth factor (EGF), fibroblast growth factor (FGF), transforming growth factor β (TGFβ), and hepatocyte growth factor (HGF).

The mimetic second messenger is a low molecular weight phosphoglycokine that is or that mimics a phosphorylated inositolglycan (IPG) of mammalian origin.

The invention further provides a use of an insulin mimetic second messenger derived from a mycobacterium, preferably *Mycobacterium vaccae*, in the preparation of a medicament for the treatment of Type I or Type II diabetes mellitus, polycystic ovary syndrome, lipodystrophy, age-related memory loss, and post-ischaemic damage secondary to stroke or post-transplant complications.

The invention further provides a use of a nerve or neurite growth factor mimetic second messenger derived from a mycobacterium, preferably *Mycobacterium vaccae*, in the preparation of a medicament for the treatment of nerve, spinal cord or central nervous system damage secondary to trauma, or autoimmune or metabolic damage, or post-ischaemic damage secondary to stroke or post-transplant complications.

The invention also provides a use of a hepatocyte growth factor mimetic second messenger derived from a mycobacterium, preferably *Mycobacterium vaccae*, in the preparation of a medicament for the treatment of hepatic damage caused by infection, alcohol abuse, drug sensitivity, or autoimmunity.

The invention also provides a use of a fibroblast growth factor mimetic second messenger and an epidermal growth factor mimetic second messenger derived from a mycobacterium, preferably *Mycobacterium vaccae*, in the preparation of a medicament for the promotion of wound healing following surgery or trauma or tissue damage induced by ischaemia or autoimmunity.

The invention also provides a use of an adrenal cell growth factor mimetic second messenger and an ACTH mimetic second messenger derived from a mycobacterium, preferably *Mycobacterium vaccae*, in the preparation of a medicament for the treatment of disease states involving adrenal atrophy such as tuberculosis.

The invention further provides a pharmaceutical composition comprising a hormone or growth factor mimetic second messenger as defined herein.

The invention also provides methods of treatment of (i) type I or type II diabetes mellitus, polycystic ovary syndrome, lipodystrophy, age-related memory loss and post-ischemic damage secondary to stroke or post-transplant complications, which comprises administering an insulin mimetic second messenger derived from a microorganism of the genus Mycobacterium, preferably *M. vaccae*;

(ii) nerve, spinal chord or central nervous system damage secondary to trauma, autoimmune or metabolic damage, or post-ischaemic damage secondary to stroke or post-transplant complications which comprises administering a nerve or neurite growth factor mimetic second messenger derived from a microorganism of the genus Mycobacterium, preferably *M. vaccae*;

(iii) hepatic damage caused by infection, alcohol abuse, drug sensitivity or autoimmunity which comprises administering a hepatocyte growth factor mimetic second messenger derived from a microorganism of the genus Mycobacterium, preferably *M. vaccae*;

(iv) a disease state involving adrenal atrophy, such as tuberculosis, which comprises administering an adrenal cell growth factor mimetic second messenger and an ACTH mimetic second messenger derived from a microorganism of the genus Mycobacterium, preferably *M. vaccae*.

The invention also further provides (v) a method for the promotion of wound healing following surgery or trauma or tissue damage induced by ischaemia or autoimmunity which comprises administering a fibroblast growth factor mimetic second messenger and an epidermal growth factor mimetic second messenger derived from a microorganism of the genus Mycobacterium, preferably *M. vaccae*.

Cell Signalling

A number of examples of cell-signalling arrangements have been described in the literature. At least three classes of cell surface receptors are involved in cellular regulation. A single transmembrane spanning domain and multiple membrane-spanning domains are described by Lowe, D. G. in EMBO (1989) 8, 1377–1384. Domains with GPI membrane anchors are described by Bamezai and Rock in Oncogene (1991) 6, 1445–1451.

The receptor tyrosine kinases (TRK), including the insulin receptor require ligand-stimulated kinase activity for a biological response, according to Lammers in EMBO (1989) 8, 1369–1375. Protein-protein interactions which occur beyond kinase activation have been described in detail for a number of growth factor specific receptors. These can broadly be classified into pathways which result in the translocation of activated protein kinases into the nucleus where they phosphorylate and activate nuclear transcription factors such as described by Egan and Weinberg in Nature (1993) 365, 781–783, or those which involve phosphorylation and activation of transcription factor subunits in the cytoplasm which then translocate to the nucleus and induce transcription as described by e.g. Muller in Nature (1993) 366, 129–135.

i) Inositolphosphoglycan second messengers are released from the cell and are active when added extracellularly None of the currently described signalling pathways can explain the community effect whereby a critical density of cells is required before a biological response can be supported. This common biological phenomenon suggests the existence of an extracellular loop involved in cell signalling. It has previously been reported that, upon growth factor stimulation, low molecular weight non-peptide factors are released into the medium. These factors are then able to mimic some of the actions of that growth factor when added to unstimulated cells. These can therefore be regarded as "second messengers". Preliminary structural analysis has suggested that these compounds contain inositol, carbohydrates and phosphate groups, and these compounds have recently been classified as A or P-type inositolphosphoglycans (as defined below). These compounds are in the family of phosphoglycokines (PGK), defined as biologically active low molecular weight compounds containing phosphorylated carbohydrates. It has been shown for example by Rademacher et al in Brazilian J. Med. Biol. Res. (1994) 27, 327–341, that the precursor forms of the IPGs are glycosylphosphatidylinositols (GPIs).

ii) Integration of growth factor and soluble mediator dependent signalling Pathways Many cytokines and growth factors share common signal transduction pathways. It has been proposed that the specificity for each factor could be achieved through unique tyrosine-phosphorylated proteins triggered by individual factors. Alternatively a number of accessory signalling pathways have also been described which give rise to a number of soluble mediators such as cAMP, IP3, $Ca+^2$, cGMP, diacylglcerol and cADPR. Growth factor and soluble mediator-dependent signalling pathways may converge to synergistically stimulate gene expression (e.g. FGF and cAMP). It has recently been suggested by Tan et al in Mol. Cell Biol. (1994) 14, 7546–7556 that, in addition to the IPGs, cADPR is also released extracellularly. In the cases of both IPGs and cADPR, it is not yet known how they reach their intracellular targets.

iii) Inositolphosphoglycans are involved in the action of many different growth factors and hormones Inositolphosphoglycan second messengers (IPGs) are able to mimic the action of a large number of insulin-dependent biological effects such as placental steroidogenesis, insulin stimulation of adipocytes, hepatocytes, myocytes and T-lymphocytes, and insulin dependent progesterone synthesis in swine ovary granulosa cells.

In addition, a number of other growth factors also appear to stimulate the production of IPGs including:

transforming growth factor β,
nerve growth factor,
hepatocyte growth factor,
insulin-like growth factor I (IGF-1),
IgE-dependent activation of mast cells,
ACTH signalling of adrenocortical cells,
activation of human platelets,
FSH and HCG stimulation of granulosa cells,
thyrotropin stimulation of thyroid cells,
cell proliferation in the early developing ear,
rat mammary gland,
control of human fibroblast proliferation, and
IL-2 stimulation of T and B-lymphocytes.

iv) A and P-type mediators related to the action of insulin

The family of myo-inositol-containing IPGs (A-type) has the following properties or activities 1) stimulation of lipogenesis in adipocytes,
2) inhibition of cAMP-dependent protein kinase and modification of the activity of adenylate cyclase and cAMP-phosphodiesterases in order to regulate the level of cAMP in cells, thus contributing to the control of cAMP and cAMP-regulated intracellular processes, and
3) support in the growth of neurons from the chick embryo statoacoustic ganglia.

The family of chiro-inositol-containing IPGs (P-type) has the following properties or activities:

1) activation of pyruvate dehydrogenase phosphatase (PDH P'ase), glycogen synthase and other enzymes, and
2) support in the growth and differentiation (neurite outgrowth) of the neurons present in the chick statoacoustic ganglion neurons.

Both the A and P type mediators can also support the growth and proliferation of EGF(Rc) transfected NIH 3T3 cells.

v) Role of mediators in insulin signalling and type II diabetes

These compounds are important in insulin signalling. Experiments have shown that addition of antibody with anti-IPG specificity is able to block both the metabolic and mitogenic actions of insulin. Furthermore, mutant cells which are unable to synthesize IPGs respond to insulin as determined by tyrosine phosphorylation, but are not stimulated to elicit the metabolic effects of the hormone.

These compounds are also important in the pathogenesis of insulin-resistant type II diabetes. It has been recognised that diabetic GK rats have a defect in the synthesis or release of functional IPGs and that decreased urinary secretion rate of chiro-inositol is directly associated with insulin resistance in both human patients with type II diabetes and spontaneously diabetic rhesus monkeys. Furthermore, infusion of chiro-inositol into normal rats given a glucose load or streptozotocin-treated rats results in decreased plasma glucose and enhanced activity of glycogen synthase I.

The preferred mycobacterium is a strain of *M. vaccae*, most preferably that denoted by R877R isolated from mud samples from the Lango district of Central Uganda (J. L. Stanford and R. C. Paul, Ann. Soc. Belge Med, Trop. 1973, 53, 141–389). The strain is a stable rough variant and belongs to the *aurum* sub-species. It can be identified as belonging to *M. vaccae* by biochemical and antigenic criteria (R. Bonicke, S. E. Juhasz., Zentr albl. Bakteriol. Parasitenkd. Infection skr. Hyg. Abt. 1, Orig., 1964, 192, 133).

The strain denoted R877R has been deposited under the terms of Budapest at the National Collection of Type Cultures (NCTC) Central Public Health Laboratory, Colindale Avenue, London NW9 5HT, United Kingdom on Feb. 13th, 1984 under the number NCTC 11659.

The following Figures are included:

FIG. 1. EGF(Rc) transfected 3T3 cells were incubated with culture medium (control), medium plus FCS or medium plus various dilutions of liver A and P-type IPGs. Both the A and P-type IPGs were able to stimulate proliferation of the fibroblasts in serum free medium. See notes to Table 1 below for the wet weight of tissue to which these dilutions correspond.

Figure 2:
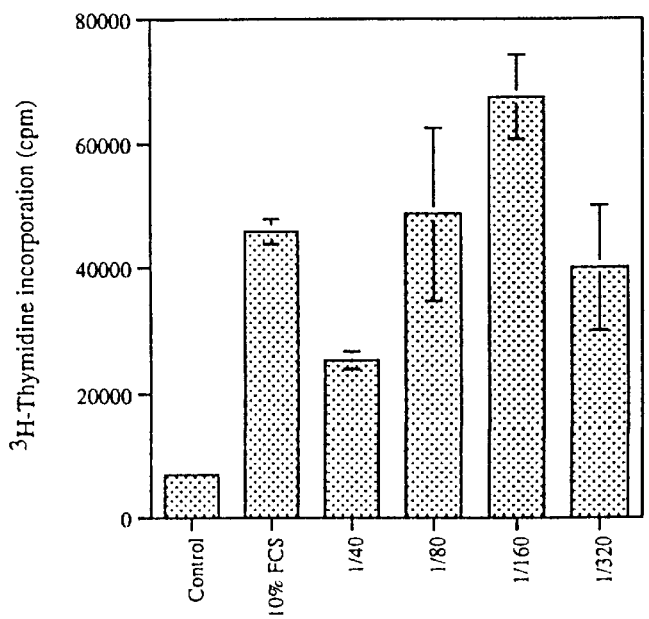
FIG. 2 is a bar graph showing various dilutions of *M. vaccae* derived PGK second messengers co-purify with liver derived A-type IPGs.

FIG. 2. EGF(Rc) transfected 3T3 cells were incubated with culture medium (control), medium plus FCS or medium plus various dilutions of *M. vaccae* derived PGK second messengers which co-purify with liver derived A-type IPGs. The *M. vaccae* derived PGK (VSB-A) at a dilution of 1/160 was as potent as a 1/40 dilution of rat liver derived IPG. See notes to Table 1 below for the wet weight of tissue to which these dilutions correspond.

Figure 3:
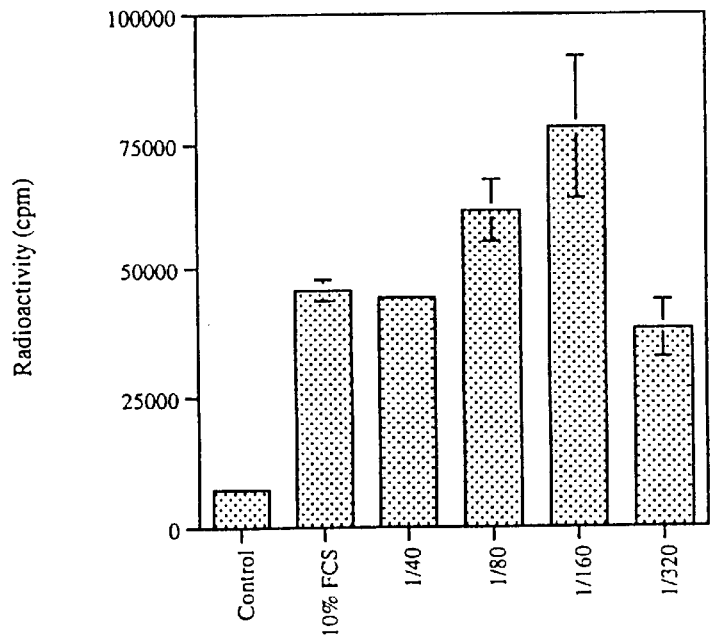
FIG. 3 is a bar graph showing various dilutions of *M. vaccae* derived PGK second messengers co-purify with liver derived A-type IPGs.

FIG. 3. EGF(Rc) transfected 3T3 cells were incubated with culture medium (control), medium plus FCS or medium plus various dilutions of *M. vaccae* derived PGK second messengers which co-purify with liver derived A-type IPGs. The *M. vaccae* derived PGK (VBS-A) at a dilution of 1/60 was as potent as a 1/40 dilution of rat liver derived IPG. See notes to Table 1 below for the wet weight of tissue to which these dilutions correspond.

Figure 4:
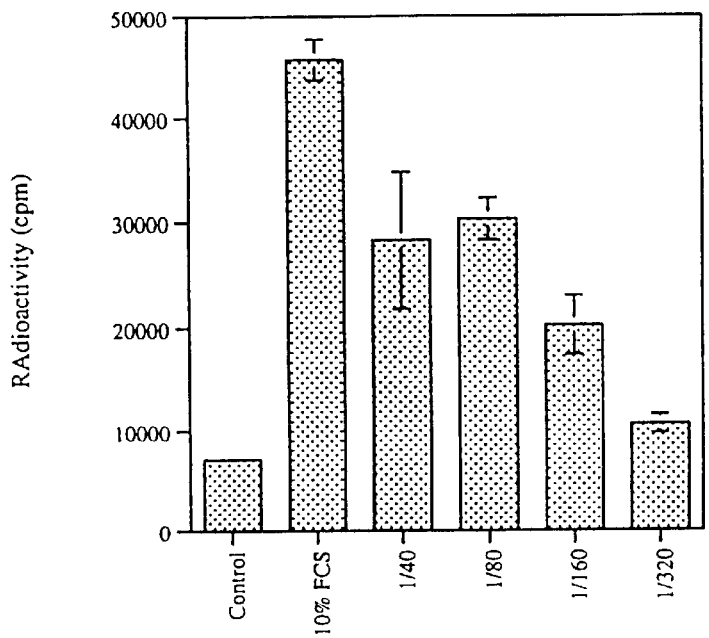
FIG. 4 is a bar graph showing various dilutions of *M. vaccae* derived PGK second messengers which co-purify with liver derived P-type IPGs.

FIG. 4. EGF(Rc) transfected 3T3 cells were incubated with culture medium (control), medium plus FCS or medium plus various dilutions of *M. vaccae* derived PGK second messengers which co-purify with liver derived P-type IPGs. The *M. vaccae* derived PGK (VBS-P) at a maximal stimulation dilution of 1/80 was not potent as 10% FCS alone. See notes to Table 1 below for the wet weight of tissue to which these dilutions correspond.

Figure 5:
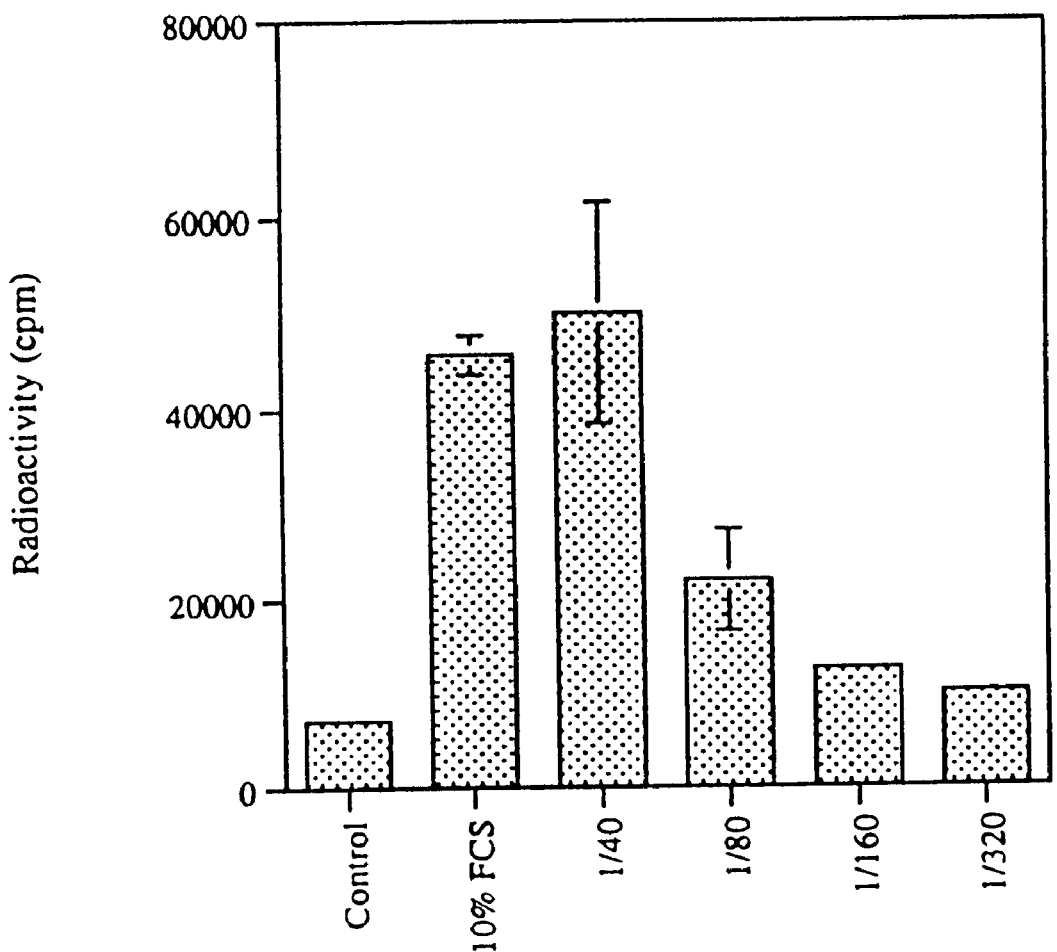
FIG. 5 is a bar graph showing various dilutions of *M. vaccae* derived PGK second messengers co-purify with liver derived P-type IPGs.

FIG. 5. EGF(Rc) transfected 3T3 cells were incubated with culture medium (control), medium plus FCS or medium plus various dilutions of *M. vaccae* derived PGK second messengers which co-purify with liver derived P-type IPGs. The *M. vaccae* derived PGK (VSB-P) at a dilution of 1/40 was not as potent as 10% FCS. See notes to Table 1 below for the wet weight of tissue to which these dilutions correspond.

Figure 6A:
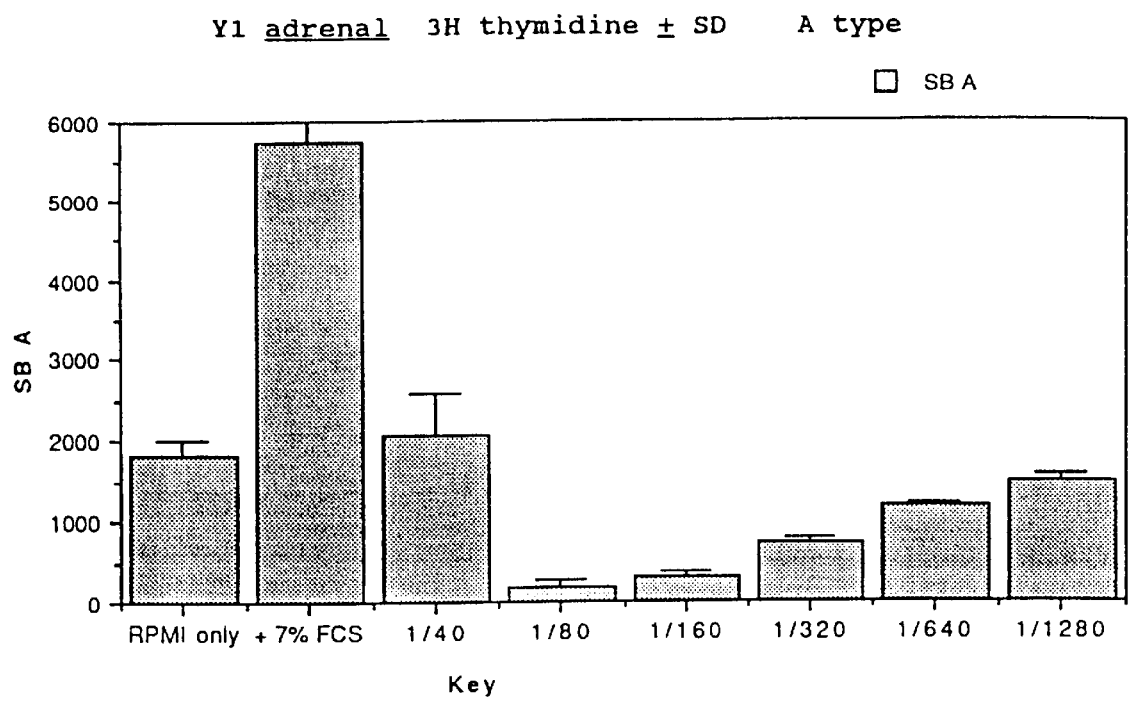
FIG. 6A is a bar graph showing the effects of low and high VSB-A concentrations on cell proliferation; culture medium (RPMI only), culture medium plus 7% FCS, or medium plus various dilutions of *M. vaccae* derived PGK second messengers which co-purify with liver derived A-type IPGs.
Figure 6B:
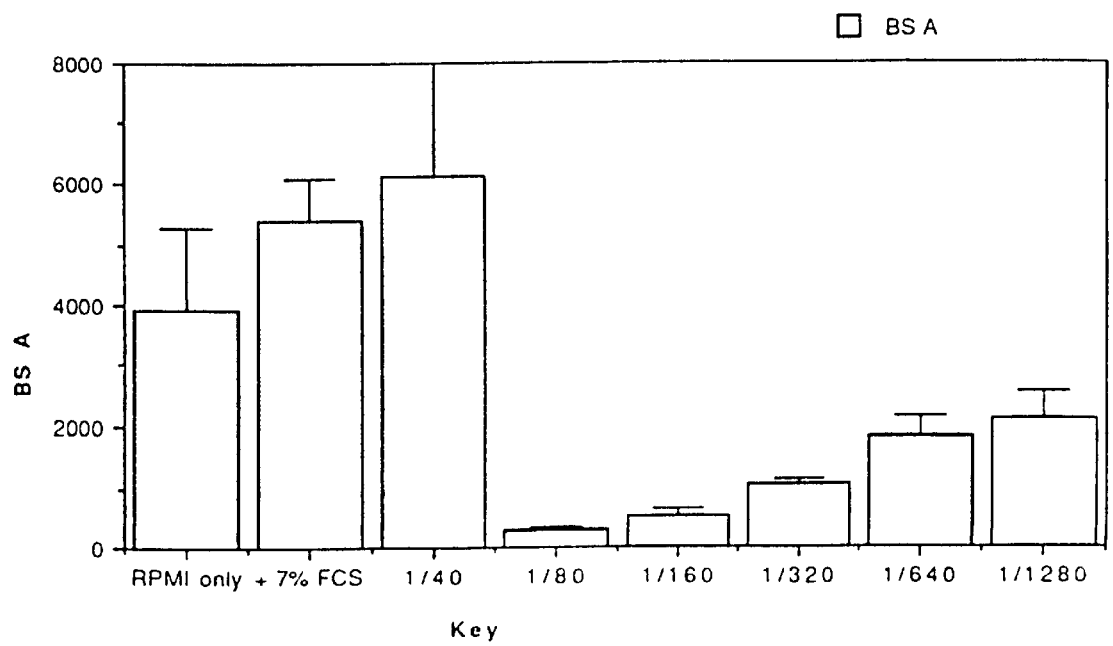
FIG. 6B is a bar graph comparing the effects of low and high VBS-A concentrations on cell proliferation.

FIG. 6, A and B. Y1 adrenal cells were incubated with culture medium (RPMI only), culture medium plus 7% FCS, or medium plus various dilutions of *M. vaccae* derived PGK second messengers which co-purify with liver derived A-type IPGs. At high concentrations (1/40) both preparations (VSB-A and VBS-A) stimulated some cell proliferation. At lower concentrations (1/80–1/1280) proliferation was inhibited. Similar patterns are seen for ACTH stimulation of the Y1 cells where the inhibition of proliferation is accompanied by steroid production.

Figure 7A:
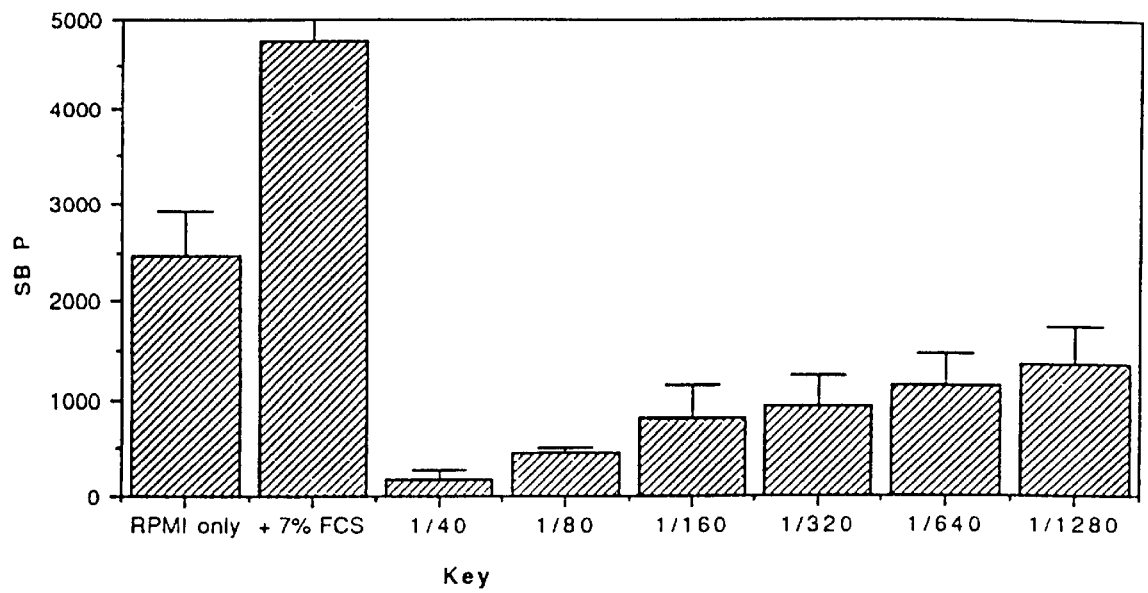
FIG. 7A is a bar graph showing VSB-P inhibited cell proliferation secondary to stimulation of steroid production and FIG. 7B is a bar graph showing VBS-P inhibited cell proliferation secondary to stimulation of steroid production.
Figure 7B:
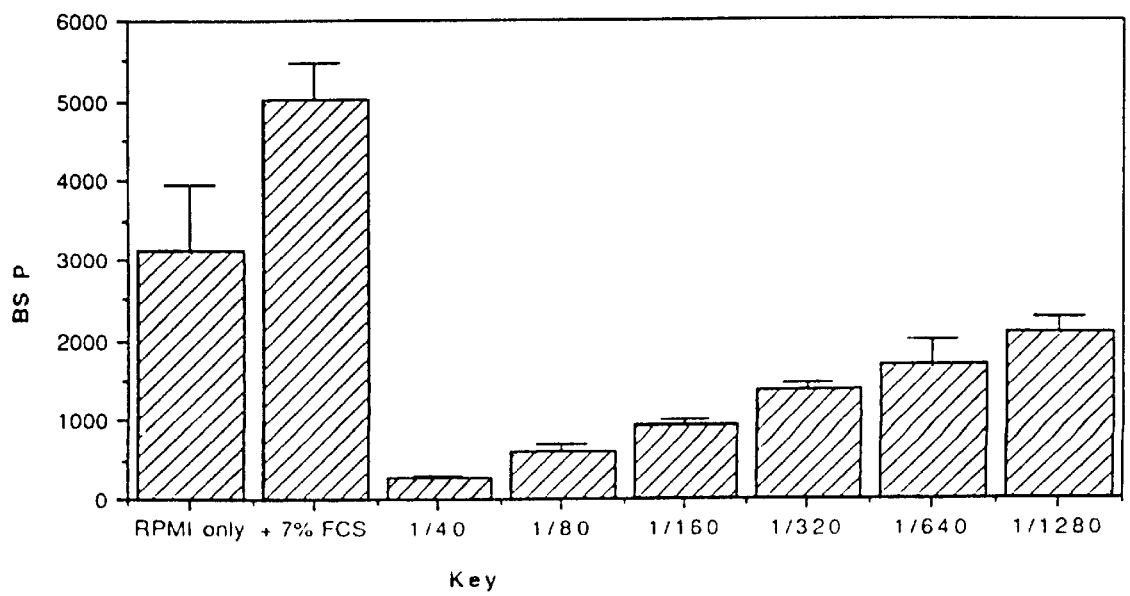

FIGS. 7A and 7B. Y1 adrenal cells were incubated with culture medium (RPMI only), culture medium plus 7% FCS, or medium plus various dilutions of *M. vaccae* derived PGK second messengers which co-purify with liver derived P-type IPGs. At all concentrations tested, both preparations (VSB-P and VBS-P) inhibited cell proliferation secondary to stimulation of steroid production. Cells were viable at all concentrations tested.

The invention is further illustrated by the following Examples.

EXAMPLES

Growth of *M. vaccae*

*Mycobacterium vaccae* NCTC11659 was grown by spreading on the surface of modified Sauton's medium, solidified with 1.5% agar. The cultures were maintained at 32° C. for 3 weeks.

Example 1

Isolation of Second Messengers from *M. vaccae*

The bacterial growth was scraped off the surface of the modified Sauton's medium with a spatula, and weighed. Bacteria were suspended in 50 mM formic acid, containing 1 mM EDTA and 1 mM β-mercaptoethanol (3 ml of buffer per gram of organisms). Then either of the following procedures was adopted:

(i) the organisms in buffer were ultrasonically disrupted for 30 mins in a cooled glass container with the wave peak to peak distance set at 8μ. Then the sonicate was boiled for 3 mins and cooled on ice. When cool it was centrifuged at 29,500 g for 90 mins at 4° C.

(ii) the organisms in buffer were boiled for 3 mins and cooled on ice. When cool the suspension was ultrasonically disrupted for 30 mins in a cooled glass container with the wave peak to peak distance set at 8μ. Then the sonicate was centrifuged at 29,500 g for 90 mins at 4° C.

The clear supernatant from either procedure was then recovered and treated exactly as for extracts of rat or human tissues as described below.

Example 2

Isolation of Second Messengers from Mammalian Tissues and *M. vaccae*

A. Isolation of IPGs from rat or human tissues following insulin stimulation

Adult male Wistar rats are starved overnight. The rats are then anaesthetised by injection of Hypnome and 20 min later are injected via the tail vein with either 0.1 ml saline or 0.1 ml saline solution containing 50 mU of insulin. After 120 seconds the animals are sacrificed by cervical dislocation, and tissues are removed in the following order: liver, heart, adipose tissue, kidney and muscle. All tissues are immediately freeze-clamped (liquid nitrogen) and stored frozen at −80° C. The rats are still normoglycemic at the time of tissue removal.

In order to extract the IPGs released following insulin stimulation, the frozen tissue is powdered under liquid nitrogen and the tissue placed directly into boiling 50 mM formic acid containing 1 mM EDTA, 1 mM β-mercaptoethanol (3 ml of buffer per gram (wet weight) of tissue), and homogenised with an Ultra-Turrex for 30 sec and then boiled for 5 minutes. The solution is then cooled on ice and centrifuged at 29,500×g for 90 minutes at 4° C. The supernatant fraction is recovered and 10 mg/ml of activated charcoal added for 10 min with stirring at 4° C. The charcoal is removed by centrifugation at 29,500×g for 30 min. at 4° C. and the clear supernatant recovered. The solution was then diluted with 10 volumes of water and the pH adjusted to 6.0 with 10% $NH_4OH$ solution and then gently shaken overnight with AG1X8 (20–50 mesh, formate form) resin (0.3 ml resin/ml solution). The resin is then poured into a chromatography column and washed with 2 bed volumes of water followed by 2 bed volumes of 1 mM HCl. The column is then eluted with 10 mM HCl (5 bed volumes) to obtain P-type IPGs, and then 50 mM HCl (5 bed volumes) to obtain A-type IPGs. Both fractions are adjusted to pH 4.0 with 10% $NH_4OH$ solution and then dried in a rotary evaporator (37° C.). The dried material is redissolved with water and then freeze-dried and this is repeated twice. Material from two rats is normally combined and subjected to descending paper chromatography (butanol/ethanol/water 4:1:1, Whatman 3MM) for 9 hours and the material in fractions −1 to 7 cm from the origin is eluted from the paper with water. After evaporation by freeze-drying, the material is dissolved in 200 μl of Hanks solution and the pH adjusted to 7 with 1 M KOH. For the case of adipose tissue, after powderizing and boiling, the solution is cooled on ice and the same volume of chloroform is added. The suspension is then stirred for 10 min and then is centrifuged. After centrifugation, the chloroform phase is removed and discarded and the aqueous phase treated as in the case of the other tissues.

B. Isolation of second messengers from *M. vaccae*

*M. vaccae* was heat treated and then sonicated or vice versa. The extract was then placed directly into boiling 500 mM formic acid containing 1 mM EDTA, 1 mM β-mercaptoethanol (3 ml of buffer per gram (wet weight) of tissue), and homogenised with an Ultra-Turrex for 30 sec and then boiled for 5 minutes. The solution was then cooled on ice and centrifuged at 29,500×g for 90 minutes at 4° C. The supernatant fraction was recovered and 10 mg/ml of activated charcoal added for 10 min with stirring at 4° C. The charcoal was removed by centrifugation at 29,500×g for 30 min at 4° C. and the clear supernatant was recovered. The solution was then diluted with 10 volumes of water and the pH adjusted to 6.0 with 10% $NH_4OH$ solution and was then gently shaken overnight with AG1X8 (formate form) resin (0.3 ml resin/ml solution). The resin was then poured into a chromatography column and washed with 2 bed volumes of water followed by 2 bed volumes of 1 mM HCl. The column was then eluted with 10 mM HCl (5 bed volumes) to obtain PGK eluting under the same conditions as mammalian P-type IPGs and then 50 mM HCl (5 bed volumes) to obtain PGK eluting under the same conditions as mammalian A-type IPGs. Both fractions were adjusted to pH 4.0 10% $NH_4OH$ solution and dried in a rotary evaporator (37° C.). The dried material was redissolved in water and was then freeze-dried, this was repeated twice. The extracts were then subjected to descending paper chromatography (butanol/ethanol/water 4:1:1, Whatman 3MM) for 9 hours and the material in fractions −1 to 7 cm from the origin were eluted from the paper with water. After evaporation by freeze-drying, the material was dissolved in 200 μl of Hanks solution and pH was adjusted to 7 with 1 M KOH.

Example 3

In vitro Effects of M. vaccae Derived Second Messengers on Phosphatase and Kinase Activities and Lipogenesis and Comparison with Liver-Derived IPGs (a) pyruvate dehydrogenase phosphatase assay The activation is followed spectrophotometrically as described by Lilley et al. in Arch. Biochem. Biophys. Res. Commun. (1992) 166, 765–771.

(b) cAMP-dependent protein kinase assay

The inhibition of cAMP-PK is measured by following the phosphorylation of histone II by $^{32}P$-ATP.

(c) lipogenesis assay

The activation of lipogenesis is monitored by measuring the incorporation of uniformly labelled glucose into lipids of isolated adipocytes as described by Rodbell in J. Biol. Chem. (1964) 239, 375–380.

Results

Table 1 summarises the action of the M. vaccae derived IPG second messengers and compares the qualitative and quantitative pattern of activities to that of the rat liver derived IPGs. Two preparations of M. vaccae-derived PGK were used for the experiments, and similar results were obtained for both preparations. Table 1 clearly demonstrates that the M. vaccae derived PGK second messengers which co-purify with liver derived P-type IPGs are able to inhibit cAMP dependent protein kinase, stimulate pyruvate dehydrogenase phosphatase and stimulate proliferation of EGF (Rc) transfected 3T3 cells. Similarly, the M. vaccae derived PGK second messengers which co-purify with the liver derived A-type IPGs are able to inhibit cAMP dependent protein kinase, stimulate lipogenesis of rat adipocytes and stimulate proliferation of EGF (Rc) 3T3 cells.

Example 4

Stimulation of EGF Receptor Transfected 3T3 Cells by M. vaccae Derived Second Messengers in Serum Free Medium and Comparison with Liver-Derived IPGs Stock cells are grown in flasks with DMEM containing 10% FCS plus 100 units/ml penicillin, 100 μg/ml streptomycin and 2 mM glutamine until the cells approach 80–90% confluence. The cells are released from the plate using trypsin (0.25%) and $10^4$ cells are added to each well of 96 well microtiter plates in 100 μl medium. The cells are allowed to adhere for 24 hours in full medium. The medium is then removed and cells washed twice with 100 μl of Hanks solution. The cells are then incubated in DMEM without FCS for 24 hours. After 24 hours the medium is removed and DMEM containing no FCS, plus FCS, or PGK alone is added. After 18 hours, $^3H$-thymidine is added per well and incubation continued for 4–6 hours. The medium is then removed, cells washed and harvested following trypsinization. Incorporation of radioactive $^3H$-thymidine into DNA is determined by transferring cell suspensions to Whatman GF/C filter disks using a cell harvester. Radioactivity is measured by scintillation counting.

Results

FIG. 1 shows the response of EGF(Rc) transfected 3T3 fibroblasts to rat liver derived A and P-type IPGs. Both mediators at maximal concentration are more potent than 10% FCS in stimulating cell proliferation. FIGS. 2 and 3 show the effect of the M. vaccae derived PGK second messengers which co-purify with liver A-type IPG on cell proliferation. Liver A-type IPG showed stimulation greater than that for FCS alone. Two separate preparations of M. vaccae-derived PGK gave similar results. FIGS. 4 and 5 show the effect of the M. vaccae derived second messengers which co-purify with liver P-type IPG on cell proliferation. While both M. vaccae preparations were able to stimulate cell proliferation they were not as effective as FCS alone. These results suggest that M. vaccae predominantly releases PGKs that mimic A-type second messengers, and releases lesser amounts of PGKs that mimic P-type second messengers. This pattern is found for IPG release in adipose and heart tissue following insulin stimulation (data not shown), in contrast to kidney and liver which release equal amounts of A and P-type mediators.

Example 5

Effect of M. vaccae Derived Second Messengers on Proliferation of Y1 Adrenal Cells in Serum Free Medium The Y1 cell line is derived from a murine adrenal carcinoma and expresses many of the enzymes involved in steroid biosynthesis, as well as functional adrenocorticotropin (ACTH) receptors. There is evidence that adrenal cells contain inositol phosphoglycans and that ACTH stimulates breakdown. This is followed by synthesis of phosphatidylinositolglycans in these cells. Thus it is likely that inositol-phosphoglycans can act as second messengers for this receptor. The line is maintained in RPMI 1640 tissue culture medium, supplemented with glutamine (2 mM) and 7% fetal calf serum. The cells adhere to the plastic, and before growth becomes confluent (2–4 days), the cells are harvested using 0.02% w/v EDTA and trypsin (0.025%) in phosphate-buffered saline, washed, resuspended in complete tissue culture medium and divided between 2 or 3 tissue culture flasks. For assay of PGK extracts of mycobacteria (whether of the type that elute under the same conditions as A-type or P-type mammalian IPG), cells are harvested as described above and are then plated into the wells of 96 well microtiter tissue culture plates, $10^4$ cells in 100 μl of RPMI 1640 plus glutamine and FCS. After incubation for 24 hours to allow attachment of the cells to the plate, the wells are washed thoroughly with unsupplemented RPMI 1640 plus glutamine only. The medium is withdrawn and replaced with:

(i) RPMI 1640 with glutamine but no serum or serum substitute (negative control)

(ii) RPMI 1640 with glutamine and 7% FCS (positive control)

(iii) RPMI 1640 with glutamine and final dilutions of *M. vaccae*-derived PGK second messengers (for example from 1/40 to 1/320 dilution of stock solution).

After incubation for a further 18–24 hours, 0.2 $\mu$Ci of $^3$H-thymidine is added to each well in unsupplemented RPMI 1640. Incubation is continued for 8–16 hours and then the medium is withdrawn, cells are released from the plastic with EDTA/trypsin as described above, and are harvested for determination of incorporation of $^3$H thymidine into DNA by liquid scintillation counting, according to standard protocols.

Results

Y1 cells proliferate at a slow rate in serum-free medium. This is enhanced by the addition of 7% FCS as shown in FIG. 7.

The addition of P-type PGK from mycobacteria causes a progressive decrease in the proliferation of Y1 cells in the absence of serum (FIG. 7). This result is the reverse of that seen with NIH-3T3 cells transfected with the EGF receptor (see FIGS. 4 and 5).

The addition of A-type PGK from mycobacteria to Y1 cells in RPMI 1640 without serum also causes inhibition of proliferation as shown in FIG. 6, but this effect is maximal at an intermediate dilution, with less inhibition when the PGK is very concentrated or very dilute. This dose/response curve is again the reverse of that seen when the same PGK preparation is tested on the transfected NIH-3T3 cells (see FIGS. 2 and 3).

The results are summarised in the following Table:

TABLE 1

| Source of Second Messenger | PKA (% inhibition) | PDH (% stimulation) | Lipogensis (% stimulation) | EGF (Rc) 3T3 (growth) |
|---|---|---|---|---|
| VB-P | 53% | 120% | —* | n.d. |
| VBS-P | n.d. | 23% | —* | + |
| VSB-P | n.d. | 42% | —* | + |
| VB-A | 43% | 12% (n.s.) | 22% | n.d. |
| VBS-A | n.d. | —* | 95% | +++ |
| VSB-A | n.d. | —* | 100% | +++ |
| L-A | 85% | —* | 100% | +++ |
| L-P | 76% | 38% | —* | +++ |
| 10% FCS | n.d. | n.d. | n.d. | +++ |
| Insulin | n.d. | n.d. | 273% | + |
| EGF | n.d. | n.d. | n.d. | + |

VBS-P: *M. vaccae*-derived PGK, organism boiled then sonicated (mimics the action of mammalian P-type second messenger).
VSB-P: *M. vaccae*-derived PGK, organism sonicated then boiled (mimics the action of mammalian P-type second messenger).
VBS-A: *M. vaccae*-derived PGK, organism boiled then sonicated (mimics the action of mammalian A-type second messenger).
VSB-A: *M. vaccae*-derived PGK, organism sonicated then boiled (mimics the action of mammalian A-type second messenger).
VB-P: *M. vaccae*-derived PGK, organism boiled (mimics the action of mammalian P-type second messenger).
VB-A: *M. vaccae*-derived PGK, organism boiled (mimics the action of mammalian A-type second messenger).
L-A: Liver A-type IPG.
L-P: Liver P-type IPG.
NOTES:
*A-type is not active in PDH assay; P-type is not active in lipogenesis assay.
n.d. Not determined.
+++ Proliferative data reported in FIGS. 1 to 5. All data were obtained in the absence of 10% FCS unless indicated otherwise.
n.s. Not significant.

For rat liver tissue, the material extraced from 16 g (wet weight) is dissolved in 0.2 ml of Hanks buffer (stock). Therefore, 10 $\mu$l of stock represents the amount of mediator recovered from 800 mg of starting tissue (wet weight).

For the lipogenesis assay, 10 $\mu$l of the stock solution is added to a final volume of 1.25 ml.

For the PDH assay, 10 $\mu$l of the stock solution is added to a final volume of 0.27 ml.

For the PKA assay, 10 $\mu$l of the stock solution is added to a final volume of 0.1 ml.

For the cell proliferation assays, the dilutions quoted are final dilutions. For example, 2.5 $\mu$l of the stock solution is added to a final volume of 0.1 ml, or 1/40 final dilution.

For *M. vaccae*, 10 $\mu$l of stock solution represents the amount of mediator recovered from 800 mg wet weight of bacteria. The amounts used in the assays are as described above for the rat liver tissues.

What is claimed is:

1. A hormone or growth factor mimetic second messenger consisting essentially of at least one phosphoglycokine isolated from a microorganism of the genus Mycobacterium.

2. A mimetic second messenger according to claim 1, which mimics the action of insulin, adrenocorticotrophic hormone (ACTH), nerve growth factor (NGF), epidermal growth factor (EGF), fibroblast growth factor (FGF), transforming growth factor $\beta$ (TGF$\beta$) or hepatocyte growth factor (HGF).

3. A mimetic second messenger according to any of claim 1 wherein the mycobacterium is *Mycobacterium vaccae*.

4. A pharmaceutical composition comprising a hormone or growth factor mimetic second messenger according to claim 1.

5. A method of treatment of type I or type II diabetes mellitus, polycystic ovary syndrome, lipodystrophy, age-related memory loss and post-ischemic damage secondary to stroke or post transplant complications which method comprises administering an effective amount of an insulin mimetic second messenger consisting essentially of at least one phosphoglycokine isolated from a microorganism of the genus Mycobacterium to a patient in need thereof.

6. A method of treatment of nerve, spinal chord or central nervous system damage secondary to trauma, autoimmune or metabolic damage, or post ischemic damage secondary to stroke or post-transplant complications, which method comprises administering an effective amount of a nerve or neurite growth factor mimetic second messenger consisting essentially of at least one phosphoglycokine isolated from a microorganism of the genus Mycobacterium to a patient in need thereof.

7. A method of treatment of hepatic damage caused by infection, alcohol abuse, drug sensitivity or autoimmunity, which method comprises administering an effective amount of a hepatocyte growth factor mimetic second messenger consisting essentially of at least one phosphoglycokine isolated from a microorganism of the genus Mycobacterium to a patient in need thereof.

8. A method of promotion of wound healing following surgery or trauma or tissue damage induced by ischemia or autoimmunity, which method comprises administering an effective amount of a fibroblast growth factor mimetic second messenger consisting essentially of at least one phosphoglycokine and an epidermal growth factor mimetic second messenger isolated from a microorganism of the genus Mycobacterium to a patient in need thereof.

9. A method of treatment of a disease state involving adrenal atrophy, which method comprises administering an effective amount of an adrenal cell growth factor mimetic second messenger consisting essentially of at least one phosphoglycokine and an ACTH mimetic second messenger isolated from a microorganism of the genus Mycobacterium to a patient in need thereof.

10. The method according to claim 9 wherein the disease state is